(12) United States Patent
Zapata

(10) Patent No.: US 8,191,190 B2
(45) Date of Patent: Jun. 5, 2012

(54) DEFLECTION COMPENSATING MECHANISM FOR PATIENT IMAGING TABLE

(75) Inventor: Jorge Zapata, Tracy, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 300 days.

(21) Appl. No.: 12/466,523

(22) Filed: May 15, 2009

(65) Prior Publication Data

US 2010/0287703 A1    Nov. 18, 2010

(51) Int. Cl.
*A61B 6/04* (2006.01)
(52) U.S. Cl. ................................. 5/601; 5/600; 378/209
(58) Field of Classification Search .............. 5/601, 600; 378/209, 208
See application file for complete search history.

(56) References Cited

U.S. PATENT DOCUMENTS

| | | | |
|---|---|---|---|
| 4,475,072 A * | 10/1984 | Schwehr et al. | 318/602 |
| 5,448,607 A | 9/1995 | McKenna | |
| 6,574,808 B1 | 6/2003 | Brown et al. | |
| 6,895,105 B2 | 5/2005 | Wollenweber | |
| 7,020,315 B2 | 3/2006 | Vaisburd et al. | |
| 7,043,784 B2 | 5/2006 | Plannerer | |
| 7,065,813 B2 | 6/2006 | Hoth et al. | |
| 7,181,792 B2 | 2/2007 | Nakamura et al. | |
| 7,186,024 B2 | 3/2007 | Varadharajulu | |
| 2004/0261176 A1 * | 12/2004 | Plannerer | 5/601 |
| 2005/0084074 A1 * | 4/2005 | Varadharajulu | 378/209 |
| 2006/0184012 A1 | 8/2006 | Marzendorfer | |
| 2006/0193443 A1 | 8/2006 | Reger | |
| 2007/0003020 A1 | 1/2007 | Hsieh et al. | |
| 2007/0094797 A1 | 5/2007 | Bartels et al. | |
| 2010/0287703 A1 * | 11/2010 | Zapata | 5/601 |

FOREIGN PATENT DOCUMENTS

JP    2006110233 A    5/2009

* cited by examiner

*Primary Examiner* — Robert G Santos

(57) ABSTRACT

When inserting a patient into a bore of a patient imaging device (e.g., CT, SPECT, PET, MRI, fMRI, etc.), a cantilevered pallet supported by an adjustable table deflects under the patient's weight. A pair of springs couples the table to first and second support arms, which are coupled to each other at a pivot point. A lever is coupled to the front end of the table and pivots on a fulcrum. A pair of wires are coupled to a rearward end of the lever and passed over respective pulleys before being coupled to a rearward portion of the table. A component of the patient's weight applied to the front edge of the table causes the lever to pivot on its fulcrum, raising the forward ends of the wires, which pass over the pulleys and pull the rearward end of the table downward to maintain the patient at a desired altitude and/or angle.

17 Claims, 5 Drawing Sheets

DEFLECTION COMPENSATING MECHANISM FOR PATIENT IMAGING TABLE

The present application finds particular application in computed tomography (CT), single photon emission computed tomography (SPECT), positron emission tomography (PET), magnetic resonance imaging (MRI) and/or variants thereof, combinations of two or more of the foregoing modalities, and/or other radiographic and nuclear imaging devices or techniques. However, it will be appreciated that the described technique(s) may also find application in other types of imaging systems and/or other patient scanning systems or techniques.

One conventional medical imaging system includes a gantry and a patient table. The table includes a base and a patient pallet cantilevered from the base into the gantry bore. Due to the size and weight of the patients, the vertical position of a patient often shifts with respect to the imaging gantry while traveling on the cantilevered pallet towards or through the gantry bore. This shift is due to the patient table sagging (deflection) while supporting the patient weight on cantilever. One compensation for this sagging problem is a catcher that receives the patient pallet as it emerges from the gantry, which increases complexity associated with height adjustment of the pallet and accounting for patient height, in addition to reducing patient comfort and adding system bulk. When the height of the pallet is raised or lowered at the base, a corresponding height adjustment is made at the catcher.

To minimize the possibility of the patient changing its relative position on the vertical axis with respect to the imaging gantry, patient imaging tables are often undesirably thick and are built out of dense materials that attenuate the patient image while providing the stiffness to support the patient. Other attempts have been made to stiffen thin pallets with a support rod or beam running the length of the pallet. While increased stiffness may be achieved in this manner, the rod increases interference in image data.

On one hand, the weight of Americans is increasing, which further increases deflection. On the other hand, the resolution of the scanners is improving, making them more sensitive to the deflection, particularly in multi-modality imaging or in imaging elongated sections in which image segments are melded together.

The present inventors have devised a unique structure and method that address these divergent issues.

In accordance with one aspect, a patient support table system includes a table portion that supports a patient pallet for longitudinal translation to cantilever the pallet from the table portion, patient weight causing a cantilevered portion of the pallet to deflect axially. The patient support table further includes a first means for generating electrical or mechanical feedback indicative of pallet deflection, and a second means for tilting the table portion to compensate for the pallet deflection.

In accordance with another aspect, a patient support apparatus includes a table portion that supports a patient pallet for longitudinal translation to cantilever the pallet from the table portion, patient weight causing a cantilevered portion of the pallet to deflect axially, a first spring and a second spring, which couple support arm and support arm, respectively, to the table portion, and a potentiometer that is coupled to the first spring and measures compression thereof. The patient support apparatus further includes a sensor that senses deviation in altitude or angle of a patient on the pallet from a desired altitude or angle as the pallet longitudinally translates an examination region. A lever pivots on a fulcrum to pull a pair of wires over a pair of pulleys to exert a downward force on a rearward portion of the table portion such that the table portion is tilted to compensate for deflection of the pallet in the examination region. The apparatus further includes a rearward elevator and a forward elevator, each of which is coupled to a respective servo for tilting the table portion to compensate for pallet deflection.

In accordance with another aspect, a method of method of maintaining a patient at a constant vertical positioning in an examination region of an imaging device, includes monitoring an altitude and angle of a cantilevered pallet supporting a patient in the examination region of the imaging device, and receiving electrical or mechanical feedback information related to the altitude and angle of the pallet longitudinally translates the patient through the examination region. The method further includes identifying a deviation of at least one of the altitude or angle of the pallet from a desired altitude and angle due to deflection of the pallet, and adjusting at least one of an altitude or angle of a table portion supporting the pallet as the pallet, such that the patient is maintained at a constant desired altitude and angle as the pallet translates the examination region.

Yet another aspect relates to a system for diagnostic imaging support system, including a processor or means for monitoring a height of a volume of interest on a pallet as the pallet traverses an examination region in a nuclear imaging device, and a processor or means for detecting a deviation in the height of the volume of interest from a desired height. The system further includes a processor or means for analyzing an amount of deflection of the pallet, and a processor or means for analyzing a height of a table on which the pallet is cantilevered into the examination region. Additionally, the system includes a processor or means for controlling at least one of angle and altitude of the table to account for deflection of the pallet to maintain the volume of interest at a constant height in the examination region.

One advantage resides in the elimination of the catcher for the pallet.

Another advantage resides in improved image quality and reduced artifact occurrences.

Another advantage resides in a thinner pallet.

Another advantage resides in improved data registration consistency, with fewer adjustments and calibration points.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

Figure 1:
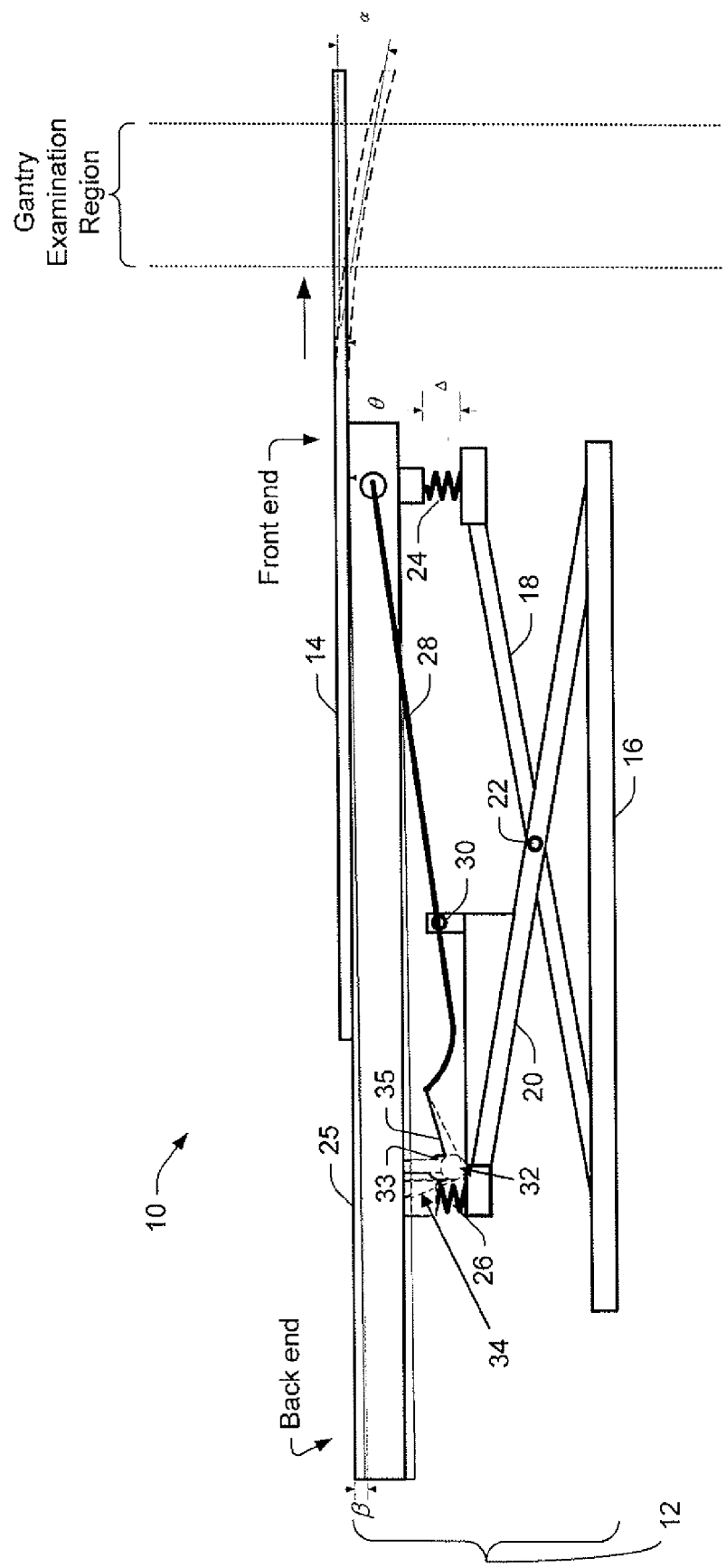
FIG. 1 illustrates a patient support table (PST) that mechanically converts force exerted by the patient's weight to proportionally compensate for sag caused by the patient's weight.

FIG. 1 illustrates a patient support table (PST) that mechanically converts force exerted by the patient's weight to proportionally compensate for sag caused by the patient's weight. The PST facilitates overcoming patient position shifting due to table sagging by compensating that change with a set of levers and pulleys that pull down a rear portion of, or cant, the table support proportionally to the weight applied to the leading edge of the table and the distance to the imaging region, bringing the front side upward, and thereby maintaining a substantially constant altitude on the vertical axis for the patient body. In this manner, the portion of the patient at the center of the examination region remains horizontal and at a constant vertical position, e.g., centered, in the examination region. For instance, displacement of the patient in a vertical direction (e.g., due to pallet deflection) by as little as a few millimeters can detrimentally affect image registration and can cause undesirable image warping. Accordingly, the systems and methods described below maintain a patient in a substantially constant altitude or angle as the patient passes through an imaging device while accounting for pallet deflection, which permits a thinner pallet to be employed and thus reduces interference caused by the pallet. Additionally, the mechanisms described herein do not require patient weight to be measured, but rather can operate without manual patient-specific adjustments prior to operation. Moreover, the PST mitigates a need for a catcher, although such may be employed in conjunction with one or more embodiments described herein for longer examination regions, such as may occur during a multimodal scan. In one embodiment, a fixed catcher is employed. In another embodiment, the catcher is adjustable.

The PST 10 comprises a base unit 12 that supports a movable pallet 14 on which a patient is positioned for moving into the examination region of a gantry. The PST further includes a lower support element 16, coupled to first and second support beams 18 and 20, which are also coupled to each other at a pivot point 22. A first spring 24 couples an upper end of the first support beam to a table 25, and a second spring 26 attaches an upper end of the second support beam to the table. A lever 28 is attached to the front end of the table and pivots on a fulcrum 30 mounted on the support beam 20 to provide mechanical feedback information. The lever is of a length proportional to a maximum weight to be supported by the table. For example, a table designed to support up to 400 pounds can be constructed with a shorter lever than a table designed to support 500 pounds. A pulley 32 is mounted on the support beam 20 in front of the second spring 26, and a wire 34 is attached adjacent one end to the table, e.g., even with the second spring 26. The other end of the wire is attached to the rearward end of the lever.

When the pallet travels towards the gantry, a component of the patient's weight is applied to the front edge of the table; this component of the weight compresses the spring 24, which moves the end of the lever 28 downwards, pivoting on the fulcrum 30, thus pulling the wire 34 over the pulley 32. This in turn pulls the rear end of the table downward by an angle β, thereby adjusting the traveling plane of the pallet in such a way that it compensates for the deflection (α) of the suspended portion of the pallet (e.g., the portion extending off of the table 25). In one embodiment, a pair of wires 34, 35 are coupled to the rearward tip of the lever and pulled over respective pulleys 32, 33. The rearward end of each wire is then coupled to the rearward portion of the table, one on each side of the second spring 26. In another embodiment, a single wire is connected to the rearward end of the lever, approximately at the center of the wire, and the two portions of the wire, segmented by the end of the lever, are passed over the pulleys 32, 33. The ends of the wire are then coupled to the bottom of the rearward portion of the table 25 on either side of the second spring 26.

As the pallet 14 moves further off of the table, the component of the patient's weight that is exerted on the front end of the table increases. This in turn increases the compression, A, of the spring 24, which pushes the forward end of the lever 28 downward. The further downward the forward end of the lever is pushed, the greater the rise of the rearward end of the lever. As the rearward end of the lever rises, more force is applied to the wire, and this force is redirected by the pulley to pull the back end of the table further downward. The downward force of the wire on the back end of the table is thus proportional to the downward force of the component of the patient's weight that is applied to the front end of the table, keeping the table level in the examination region of the gantry.

According to an example, spring 24 compresses by an amount Δ (e.g., approximately 1.5 cm) in response to a given weight component exerted on the front end of the table, and the pallet flexes (e.g., approximately 10°). The compression causes the lever to pivot such that when the rear end of the lever is raised, a force is applied to the wire, redirected by the pulley, to pull the back end of the table downward by and amount β (e.g., approximately 0.7°). It will be appreciated that the foregoing example is illustrative in nature, and that the values (e.g., distances, angles, etc.) are not intended to be construed in a limiting sense.

Figure 2:
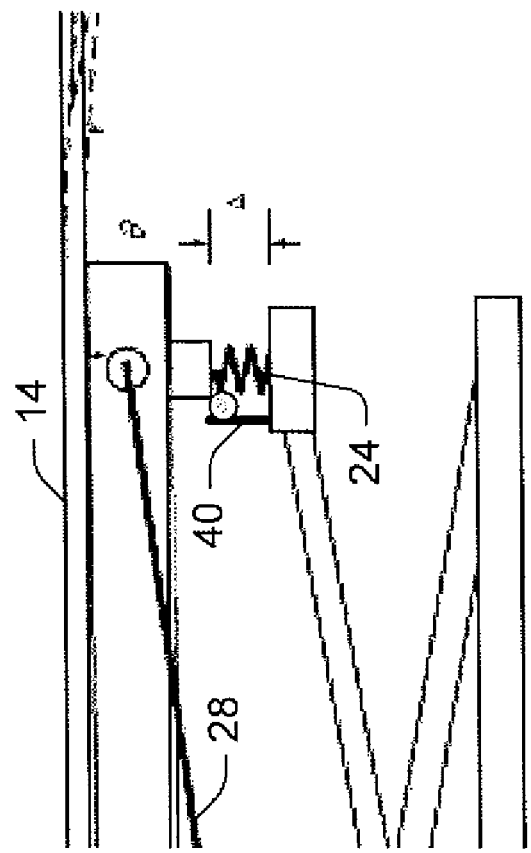
FIG. 2 illustrates another embodiment of the PST, in which a potentiometer is coupled to the forward spring to provide feedback information related to spring compression, which is indicative of an amount of weight being exerted on the leading edge of the table.

FIG. 2 illustrates another embodiment of the PST 10, in which a potentiometer 40 is coupled to the forward spring 24 to provide electrical feedback information related to spring compression, which is indicative of an amount of weight being exerted on the leading edge of the table. For instance, as the pallet 14 moves forward, a greater portion of the patient's weight is applied to the leading edge of the table relative to the lagging, or rearward, edge of the table. Since the spring constant of the spring 24 is known, the distance by which the spring is compressed can be used to determine the magnitude of force exerted on the leading edge due to the patient's weight. Thus, the magnitude of the patient's weight exerted on the leading edge can be determined. The table can then be adjusted accordingly to ensure that the altitude and/or angle of the patient is kept constant in the examination region of the gantry. For example, the delta compression of the spring 24 at the leading edge of the table can be compensated by elevating the table altitude position. That is, the compression distance can be measured by the potentiometer 40 and fed back to a motion control system to adjust the table altitude and/or tilt accordingly.

Figure 3:
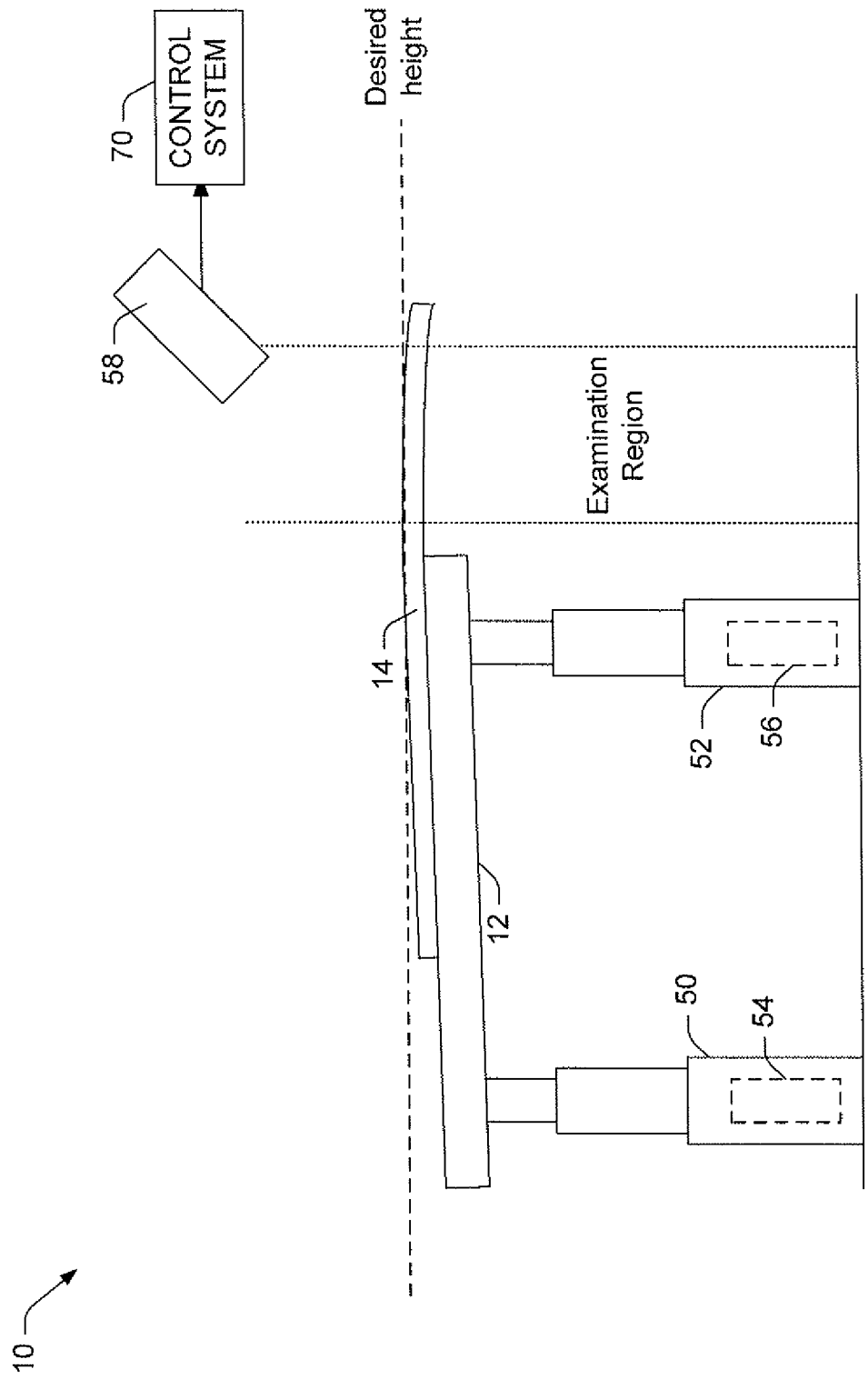
FIG. 3 illustrates another embodiment of a PST with variable height capability in which a forward portion or all of a table is raised to compensate for patient pallet sagging due to a patient's weight component on the unsupported portion of the pallet.

FIG. 3 illustrates another embodiment of a PST with variable height/tilt capability in which a forward portion or all of a table is raised to compensate for patient pallet sagging due to a patient's weight component on the unsupported portion of the pallet. For example, the cantilevered patient pallet 14 is supported on a dual elevator table mechanism. That is, the patient table 25 includes front and rear elevators 50 and 52 for raising and lowering the patient pallet and/or the table on which the pallet rests. The table elevators 52, 54 can be used in conjunction with the PST 10 and associated components as described with regard to FIGS. 1 and 2. According to another embodiment, the table elevators are employed without the lever, springs, pulley(s), etc. A computer control algorithm is used to control servomotors 54, 56 for these elevators to provide an analogous counter-canting of the foot end of the patient pallet to keep the portion of the patient in the center of the examination region horizontal and at a constant altitude. Other actively controlled systems for causing this counter-canting are also contemplated. In other embodiments, both elevators are employed concurrently to raise the table, thus keeping the table level while compensating for pallet deflection in the examination region.

Further, the amount by which the patient pallet is sagging at the center of the examination region can be determined in various ways. For example, it can be determined by the weight of the patient and the extent to which the patient pallet is cantilevered. Alternately, it can be actively measured with a laser or video camera 58. As yet another alternative, the reconstructed image can be monitored. As the patient pallet deflects further, the z-coordinate of the reconstructed image shifts downward.

Figure 4:
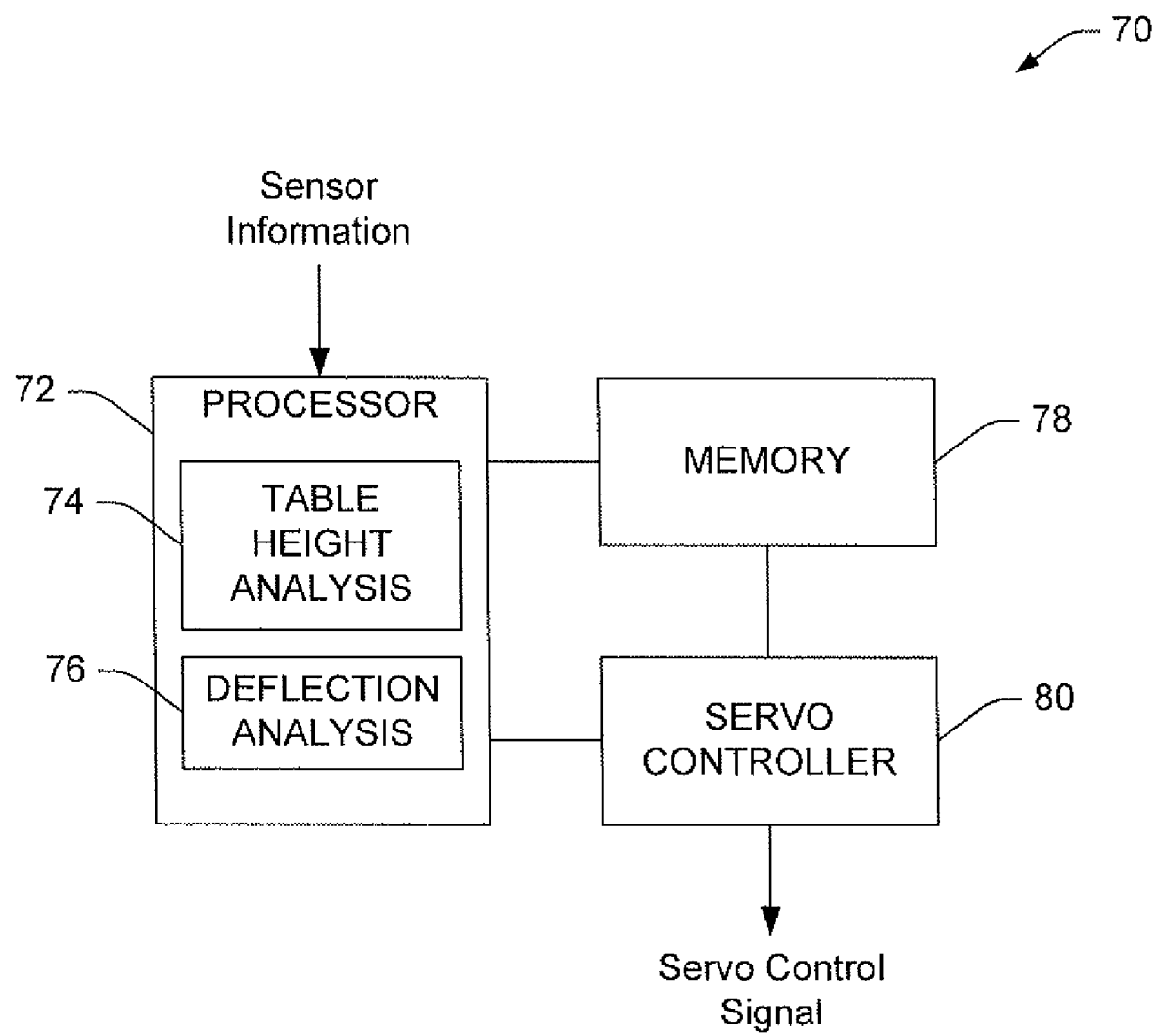
FIG. 4 illustrates a control system for controlling the PSTs described above.

FIG. 4 illustrates a control system 70 for controlling the PSTs described above. The control system includes a processor 72 that receives sensor information related to one or more of the height or altitude and/or angle of the patient table, the altitude or angle of the pallet in the examination region, the deflection or sag of the pallet, compression of spring 24, etc. In one embodiment, the sensor information is received form the potentiometer 40, and describes the compression of the spring 24. In another embodiment, the sensor information is received from a camera sensor 58 or other sensing device (e.g., laser, SPECT camera head, etc.) that monitors the altitude and/or angle of deflection of the pallet in the examination region. In another embodiment, the sensor information is received from a load cell or other device that measures weight on the forward end of the table. The processor performs table height analysis 74 to determine a height of the table and/or the height of the pallet in the examination region, and a deflection analysis 76 executed to evaluate the amount of deflection of the pallet. The deflection analysis can be performed using a camera sensor, laser sensor, SPECT camera head, or the like. Additionally or alternatively, deflection can be calculated or estimated using a deflection formula that accounts for modulus of elasticity of the pallet material, area moment of inertia of the pallet material, load on the pallet, length of the pallet extending beyond the table (e.g., span), and other factors, as is known. Sensor information, analyzed information, control signal information, lookup tables of pallet deflection under various loads and at various spans, and any other suitable information can be stored to memory 78.

Once the height of the pallet in the examination region of an imaging device (e.g., SPECT, PET, CT, MRI, fMRI, etc.) has been determined, remedial adjustments can be made to the table height and/or tilt to compensate for any detected deviation in pallet height. According to an embodiment, if the sagging of the pallet causes the patient to be 0.5 cm below a desired height, as determined by the processor 72 based on received sensor information, then a servo controller 80 can transmit an instruction to servomotor 56 to increase the height of the front of the table to a height that places the patient at the desired height in the examination region. According to another embodiment, the servo controller 80 transmits a signal to both servomotors 54, 56, instructing both motors to extend their respective elevators 50, 52 to increase table height until the patient is at the desired height in the examination region or to increase the height of the front and/or decrease the height of the rear of the table to maintain the imaged region both at a constant altitude and at a constant angle of entry (e.g., an angle to horizontal).

Figure 5:
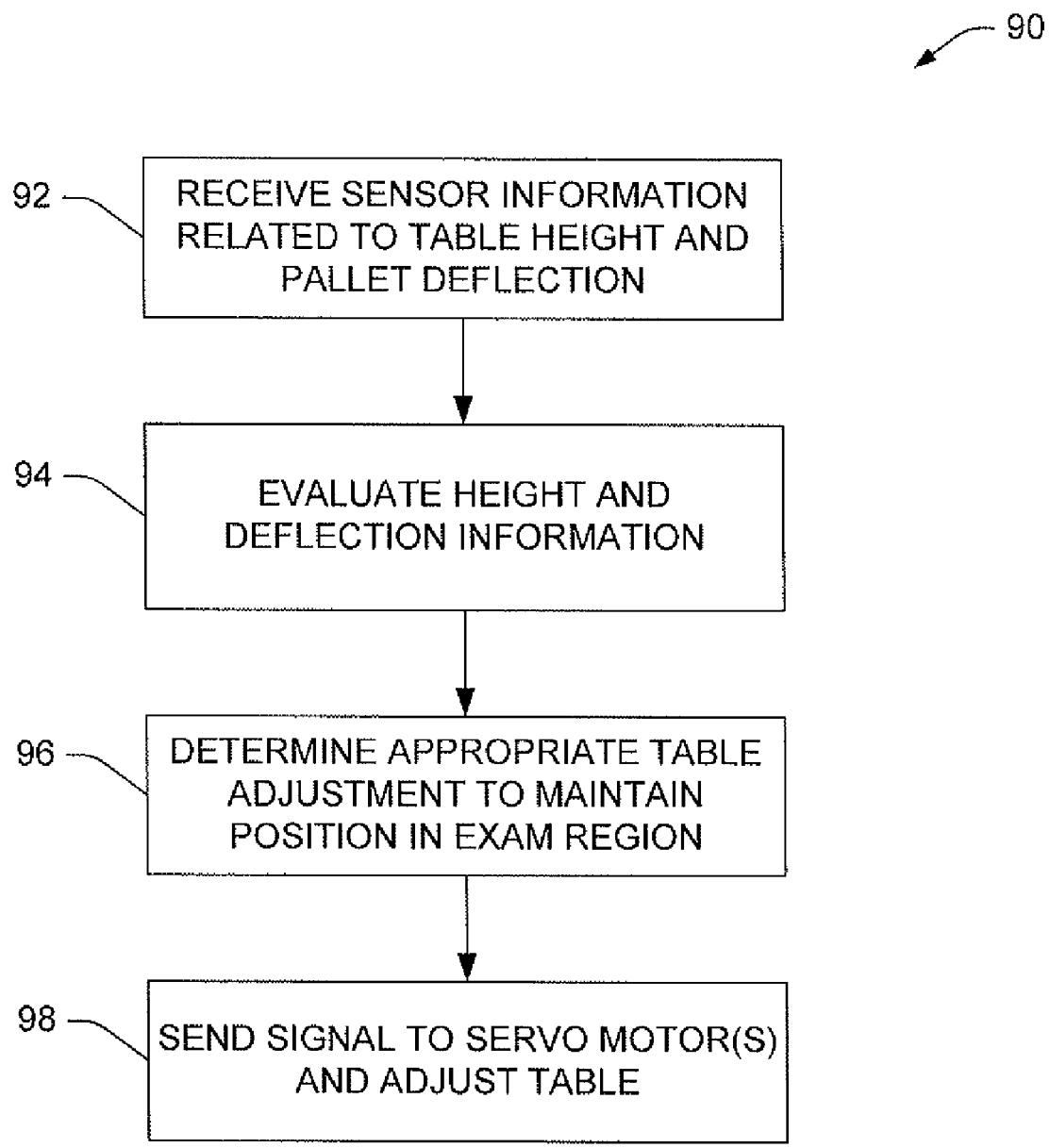
FIG. 5 illustrates a method for compensating for pallet deflection in an examination region in an imaging device (e.g., PET, CT, SPECT, MRI, fMRI, etc.) to maintain the pallet at a desired altitude and/or angle within the examination region.

FIG. 5 illustrates a method 90 for compensating for pallet deflection in an examination region in an imaging device (e.g., PET, CT, SPECT, MRI, fMRI, etc.) to maintain the pallet at a desired height within the examination region. At 92, information is received form a sensor, indicative of table height, pallet deflection, and the like. At 94, the received information is evaluated to determine whether a volume of interest on the pallet is positioned at a desired height in an examination region into which the pallet is inserted. According to one embodiment, the evaluation includes assessing whether the volume of interest is within a predetermined acceptable distance or range of the desired height. In another embodiment, the canting of the imaged region relative to horizontal is also determined. At 96, a determination is made regarding an appropriate corrective adjustment to table height, in order to compensate for pallet sagging. A control signal is sent to one or more servo motors in the patient table, which raise and/or lower one or both ends of the table to compensate for the sag of the pallet and raise the volume of interest to the desired height within the examination region, at 98.

Having thus described the various embodiments, the invention is now claimed to be:

1. A patient support table system, comprising:
   a table portion that supports a patient pallet for longitudinal translation to cantilever the pallet from the table portion, patient weight causing a cantilevered portion of the pallet to deflect axially;
   a first means for generating electrical or mechanical feedback indicative of pallet deflection;
   a second means for tilting the table portion to compensate for the pallet deflection;
   wherein the first means includes:
     a first spring that couples a front end of the table portion to a first support arm; and
     a lever, coupled to the front end of the table portion, that pivots on a fulcrum point.

2. The patient support table system according to claim 1, wherein the second means tilts the table portion such that a portion of a patient cantilevered a preselected distance from the table portion maintains a constant altitude and angle to horizontal as the pallet translates longitudinally such that a greater or smaller portion of the pallet is cantilevered from the table portion.

3. The patient support table system according to claim 1, wherein the second means includes a pair of wires with forward ends coupled to rearward end of the lever and passed over respective pulleys, with the pulleys and rearward ends of the wires coupled to a rearward portion of the table portion such that pivoting of the lever on the fulcrum causes the rearward portion of the table portion to move downward.

4. The system according to claim 3, wherein the pallet supports a patient and translates longitudinally into an examination region of a scanning device, the examination region being the preselected distance from the table portion.

5. The system according to claim 4, wherein as the pallet translates forward, the force exerted by the weight on the front end of the table portion increases and forces a front end of the lever downward, pivoting the lever about the fulcrum point and pulling substantially upward on the forward ends of the wires, the upward force exerted on the wires being converted by the pulleys to a downward force on the rearward portion of the table portion.

6. A diagnostic imaging system, comprising:
   a diagnostic imager with an examination region; and
   the patient support table according to claim 1.

7. A method of supporting a patient during an examination, comprising:

supporting a patient pallet on a table portion for longitudinal translation to cantilever the pallet from the table portion, patient weight causing a cantilevered portion of the pallet to deflect axially;

generating electrical or mechanical feedback indicative of pallet deflection, the feedback being generated via a first spring that couples a front end of the table portion to a first support arm, and a lever, coupled to the front end of the table portion, that pivots on a fulcrum point; and tilting the table portion to compensate for the pallet deflection.

8. The method according to claim 7, wherein the table portion is tilted such that a portion of a patient cantilevered a preselected distance from the table portion maintains a constant altitude and angle to horizontal as the pallet translates longitudinally such that a greater or smaller portion of the pallet is cantilevered from the table portion.

9. The method according to claim 7, further comprising pivoting the lever on the fulcrum to cause a rearward portion of the table portion to move downward via a pair of wires with forward ends coupled to rearward end of the lever and passed over respective pulleys, with the pulleys and rearward ends of the wires coupled to the rearward portion of the table portion.

10. The method according to claim 9, further comprising supporting on the pallet and translating the pallet longitudinally into an examination region of a scanning device, the examination region being the preselected distance from the table portion.

11. The method according to claim 10, wherein as the pallet translates forward, the force exerted by the weight on the front end of the table portion increases and forces a front end of the lever downward, pivoting the lever about the fulcrum point and pulling substantially upward on the forward ends of the wires, the upward force exerted on the wires being converted by the pulleys to a downward force on the rearward portion of the table portion.

12. A patient support table feedback system, comprising:
a first spring that couples a front end of a table portion to a first support arm;
a lever, coupled to the front end of the table portion, that pivots on a fulcrum point;
wherein the table portion supports a patient pallet for longitudinal translation to cantilever the pallet from the table portion, patient weight causing a cantilevered portion of the pallet to deflect axially; and
wherein the first spring and the lever cooperate to generate feedback information indicative of pallet deflection.

13. The patient support table feedback system according to claim 12, wherein the table portion is tiltable such that a portion of a patient cantilevered a preselected distance from the table portion maintains a constant altitude and angle to horizontal as the pallet translates longitudinally such that a greater or smaller portion of the pallet is cantilevered from the table portion.

14. The patient support table feedback system according to claim 12, further including a pair of wires with forward ends coupled to rearward end of the lever and passed over respective pulleys, with the pulleys and rearward ends of the wires coupled to a rearward portion of the table portion such that pivoting of the lever on the fulcrum causes the rearward portion of the table portion to move downward.

15. The system according to claim 14, wherein the pallet supports a patient and translates longitudinally into an examination region of a scanning device, the examination region being the preselected distance from the table portion.

16. The system according to claim 15, wherein as the pallet translates forward, the force exerted by the weight on the front end of the table portion increases and forces a front end of the lever downward, pivoting the lever about the fulcrum point and pulling substantially upward on the forward ends of the wires, the upward force exerted on the wires being converted by the pulleys to a downward force on the rearward portion of the table portion.

17. A diagnostic imaging system, comprising:
a diagnostic imager with an examination region; and
the patient support table according to claim 12.

* * * * *